(12) United States Patent
Koike et al.

(10) Patent No.: US 6,579,860 B1
(45) Date of Patent: Jun. 17, 2003

(54) INTERLEUKIN-6 PRODUCTION INHIBITORS

(75) Inventors: Junzo Koike, Chiba (JP); Yuriko Funaba, Kanagawa (JP); Masahiko Tanahashi, Osaka (JP); Seiji Okazaki, Kanagawa (JP); Masatoshi Ito, Kanagawa (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 09/623,014

(22) PCT Filed: Jun. 23, 1999

(86) PCT No.: PCT/JP99/03346

§ 371 (c)(1),
(2), (4) Date: Sep. 27, 2000

(87) PCT Pub. No.: WO00/38693

PCT Pub. Date: Jun. 7, 2000

(30) Foreign Application Priority Data

Dec. 25, 1998 (JP) .............................................. 10-370150

(51) Int. Cl.[7] .................... A61K 31/663; A61K 31/695; C07F 9/28
(52) U.S. Cl. ......................... 514/107; 514/63; 558/156; 558/161; 562/13
(58) Field of Search .................... 514/107, 63; 558/156, 558/161; 562/13

(56) References Cited

U.S. PATENT DOCUMENTS 5,683,992 A * 11/1997 Kawabe et al. ............... 514/63

OTHER PUBLICATIONS

Tokuda, H. et al.: Tiludronate inhibits interleukin–6 synthesis in osteoblasts. J. Cell. Biochem. vol. 69, pp. 252–259, Jun. 1, 1998.*

Monkkonen, J. et al.: Effects of Tiludronate and Ibandronate on the nsecretion of proinflammatory cytokines and nitric oxide from macrophages in vitro. Life Sci. vol. 62, pp. PL 95–102, Jan. 16, 1998.*

* cited by examiner

Primary Examiner—Charanjit S. Aulakh
(74) Attorney, Agent, or Firm—Schnader Harrison Segal & Lewis LLP

(57) ABSTRACT

An interleukin-6 production inhibitor is provided containing a methanebisphosphonic acid derivative as an active component, which has inhibitory effects on interleukin-6 production and is useful in prevention and treatment of diseases due to abnormal production of the interleukin-6. This pharmaceutical is anticipated to have effects in prevention and treatment of diseases related to the interleukin-6, for example, thrombocytosis, inflammatory diseases, abnormal immune response diseases, osteoporosis, rheumatoid arthritis, hypercalcemia, multiple myeloma, cachexia, and nephritis.

11 Claims, No Drawings

INTERLEUKIN-6 PRODUCTION INHIBITORS

This application is a 371 of PCT/JP99/03346 filed Jun. 23, 1999, now WO00/38693 Jun. 7, 2000.

TECHNICAL FIELD

The present invention relates to an interleukin-6 production inhibitor or thrombocytosis inhibitor, which contains one of methanebisphosphonic acid derivatives, and esters, salts, and hydrates thereof, as active components.

BACKGROUND ART

Cytokine is a generic name for a group of humoral factors performing main intercellular information communication, particularly in the immune response, hematopoietic reactions, and inflammation reactions. Many cytokines have been identified and functions thereof have been analyzed. As a result, it has been clarified that the action of a cytokine affects various biological functions, such as development, differentiation, and maintaining homeostasis, and that abnormally high cytokine production is deeply related to many diseases.

In particular, regarding interleukin-6, cDNA thereof was isolated in 1986 as a B-cell differentiation factor which induces final differentiation of B cells into antibody producing cells [Hirano T. et al., Nature, 324, 73–76(1986)]. Interleukin-6 is secreted from immunocytes, such as T cells, B cells, and macrophages, and various other cells, such as, fibroblasts, vascular endothelial cells, keratinocytes, and renal mesangial cells, and it is known that this exerts effects on the immune system, such as B-cell differentiation, and T cell activation and differentiation [Hirano T. et al., Immunol. Today, 11, pp. 443–449 (1990)]. In addition, interleukin-6 is deeply related to hematopoietic systems, for example, proliferating hematopoietic cells in cooperation with interleukin-3 [Ikebuchi K. et al., Proc. Natl. Acad. Sci., 84, pp. 9035–9039 (1987)]; promoting maturation of megakaryocyte and inducing an increase in platelet, as a platelet hematopoietic factor [Ikebuch K. et al., Proc. Natl. Acad. Sci., 86, pp. 5953–5957 (1989)]; and promoting differentiation of osteoclast-like multinucleated cells [Kurihara H. et al., J. Immunol., 144, pp. 4226–4230 (1990)]. Moreover, this exhibits a significant variety of functions, for example, the induction of acute phase proteins such as a 2-macroglobulin and CRP [Woloski BMR. et al., Proc. Natl. Acad. Sci., 82, pp. 1443–1447 (1985)], and participating in proliferation and differentiation of nerve cells [Hirano T. et al., Immunol. Today, 11, pp. 443–449 (1990)].

Although interleukin-6 is multi-functional factor, as described above, it has been clarified that excess production thereof is deeply related to onset, progression, and maintenance of various diseases.

For example, increased expression of messenger RNA for interleukin-6 in bone marrow of postmenopausal osteoporosis patients is reported [Raston S. H., J. Bone Miner. Res., 9, pp. 883–890 (1994)].

Moreover, the association with autoimmune diseases is reported; for example, large amounts of interleukin-6 are detected in synovial fluid and culture supernatant of synovial tissue from rheumatoid arthritis patients [Hirano T. et al., Eur. J. Immunol., 18, pp. 1797–1801 (1988)], and in systemic lupus erythematosus, production of interleukin-6 from B cells is promoted, and thus the B cells are activated by the autocrine system [Umland SP. et al., J. Immunol., 142, pp. 1528–1535 (1989)].

In addition, in multiple myeloma, interleukin-6 functions as a growth factor in myeloma proliferation [Kawano M. et al., Nature, 322, pp. 83–85 (1988); Klein B. et al., Blood, 73, pp. 517–526 (1989); Zhang X G., J. Exp. Med., 179, pp. 1337–1342 (1994); and Nishimoto N. et al., J. Exp. Med., 179, pp. 1343–1347 (1994)]. In multiple myeloma patients, interleukin-6 is considered to be produced in excess in osteoblast and stromal cells [Barille S., Blood, 86, pp. 3151–3159 (1995); and Caligaris-Capio F. et al., Blood, 77, pp. 2688–2693 (1991)].

In atrial myxoma patients, a large amount of interleukin-6 is produced in tumor cells [Kanda T. et al., Inter. J. Cardiol., 45, pp. 144–146 (1994)].

In Castleman's syndrome, a large amount of interleukin-6 is produced in hypertrophic lymph nodes and the interleukin-6 concentration in the serum is correlated to lymphadenia, hypergammaglobulinemia, and acute phase protein levels in serum [Yoshizaki K. et. al., Blood, 74, pp. 1360–1367 (1989)].

Furthermore, the correlation between the interleukin-6 and the cachexia occurring in the inflammatory reaction and tumors is reported [Oldenburg H S. et al., Eur. J. Immunol., 23, pp. 1889–1894 (1993)], [Yasumoto K. et al., Cancer Res., 55, pp. 921–927 (1995)], and the strong correlation between the interleukin-6 and the hypercalcemia due to tumors and the like is also disclosed [Strassmann G. et al., Cytokine, 5, pp. 463–468 (1993)].

Urine from primary glomerulonephritis patients has high interleukin-6 activity compared to that of healthy humans, and the interleukin-6 acts as a growth factor for renal mesangial cells [Horii Y. et al., J. Immunol, 143, pp. 3949–3955 (1989)]. Also, the activity of interleukin-6 is enhanced in serum and urine in Kawasaki's disease patients [Ueno Y. et al., Clin. Exp. Immunol, 76, pp. 337–342 (1989)].

The interleukin-6 concentration in the serum of psoriatic patients is significantly increased and expression of messenger RNA and protein of interleukin-6 are enhanced at the lesion sites [Grossman R M., et al., Proc. Natl. Acad. Sci. USA, 86, pp. 6367–6371 (1989)].

Platelet, the increasing production thereof is induced by interleukin-6, is one of blood components, which play a primary role in hemostasis mechanism, and the platelets are produced from megakaryocytes which are precursor cells in myeloid tissue. Megakaryocytes are classified into megakaryoblasts, promegakaryocytes, megakaryocytes, and platelet-producing megakaryocytes in the maturation process thereof. In the production process of the platelets, various humoral factors, that is, platelet producing factors, are related, and subtle balance therebetween maintains a constant number of platelets in blood. Examples of known platelet producing factors are interleukin-3, interleukin-7, interleukin-11, leukemia inhibitory factor (LIF), erythropoietin, and thrombopoietin.

In healthy humans, the number of platelets in peripheral blood is maintained constant by the action of the above humoral factors. When an imbalance of humoral factors occurs or an abnormallity in hematopoietic stem cells occurs for any reason, the number of the platelets in the peripheral blood increases abnormally, resulting in a state called thrombocytosis. The thrombocytosis includes primary thrombocythemia, secondary thrombocytosis, reactive thrombocytosis, and the like. The thrombocytosis involves persistently increasing platelets; thrombosis, such as peripheral ischemia and transient cerebral ischemia; and hemorrhagic diseases, such as peliosis, subcutaneous bleeding, nasal bleeding, bloody stool, gingival bleeding, and intracranial bleeding, and sometimes induces serious symptoms, such as large artery infarctions, e.g., myocardial infarction and brain infarction.

The origin of the primary thrombocythemia is clonal abnormalities in precursor cells of platelets in the myeloid tissue. Medulla depression therapies using alkylating agents such as busulphan are frequently performed for primary thrombocythemia, and the onset of carcinoma due to long-term administration of the alkylating agents is reported. Also, platelet activity reduction therapies using Aspirin or the like has been performed, and side effects, such as aggravation of hemorrhagic diseases, are also reported. Thus, no satisfactory method of treatment is established.

The reactive thrombocytosis is secondary thrombocytosis accompanying underlying diseases, such as tumors, iron deficiency, bleeding, acute inflammatory diseases, chronic inflammatory diseases, such as rheumatoid arthritis, ulcerative colitis, and osteomyelitis, and osteoporosis. Although the details of the mechanism are unclear, enhanced activity of erythropoietin is considered to be a major factor in the underlying diseases, such as bleeding and iron deficiency, and enhanced production of interleukin-6 is considered to be a major factor of the underlying diseases such as rheumatoid arthritis and tumors. Moreover, in thrombocytosis patients, a positive correlation is recognized between the number of platelets and the interleukin-6 concentration in the serum.

As described above, the interleukin-6 is deeply related to initiation, progression, and maintenance of various diseases, and pharmaceuticals suppressing the production of interleukin-6 will be significantly useful as therapeutic agents and/or prophylactic drugs for the above-mentioned diseases. At present, for example, steroid agents are known as pharmaceuticals for suppressing the production of cytokines, including interleukin-6. However, these have many problems and are still unsatisfactory since these result in digestive damage and aggravation of the general condition when administration is terminated. In therapy for reactive thrombocytosis, platelet function suppressing agents, such as Aspirin, are used when significant thrombocytosis continues for long periods or when risk factors for thrombosis, such as arteriosclerosis, are involved. However, these agents result in aggravation of hemorrhagic diseases. As a result, no satisfactory therapy is established at present.

The above diseases induced by interleukin-6 are examples and are not limiting.

On the other hand, bone resorption suppressing effects of bisphosphonic acid derivatives are known. Some of these derivatives are used for medical purposes to suppress tumor-induced osteolysis, and excessive bone resorption in Paget's disease and in osteoporosis. These compounds are disclosed in, for example, Japanese Unexamined Patent Application Publication Nos. 54-2341, 61-43196, 56-73091, and 2-288886.

In addition, Japanese Examined Patent Application Publication No. 8-26048 discloses bisphosphonic acid derivatives which are effective as anti-inflammatories, antirheumatics, improvements in bone metabolic diseases, suppression of production and activity of interleukin-1, and antioxidation. Also, Japanese Unexamined Patent Application Publication Nos. 59-42395 and 1-160993 disclose bisphosphonic acid derivatives having anti-inflammatory effects. Moreover, many other bisphosophonic acid derivatives having anti-inflammatory effects are known. For example, anti-inflammatory effects of clodronate and etidronate disclosed in [Lawrence F., Arthritis and Rheumatism, 22, 340–346, 1979].

However, the effects of the bisphosphonic acid derivatives on the production of the interleukin-6 depend significantly on the structures of the compounds. For example, clodronate suppresses cytokine production in mouse macrophage cells, but etidronate does not have such an effect. In contrast, it is reported that pamidronate enhances release of cytokine [Pannanen N. et al., Pharmaceutical Research, 12(6), 916–922, 1955]. Moreover, it is reported that the administration of alendronate to Paget's disease patients results in an increased interleukin-6 concentration in serum [Schweitzer D H. et al., J. Bone and Miner. Res. 10(6), 956–962, 1955]. Accordingly, the effects of the bisphosphonic acid derivatives on the interleukin-6 production are significantly different regardless of similarity in the structures thereof and commonality in the anti-inflammatory activities.

Japanese Examined Patent Application Publication No. 8-26048 discloses a bisphosphonic acid derivative having inhibitory effects on the production of interleukin-1, which is one type of cytokine. Individual cytokines are, however, controlled by different expression mechanisms, and the effects of this bisphosphonic acid derivative on the production of other cytokines and suppression of thrombocytosis are not clear.

It is an object of the present invention to provide a novel interleukin-6 production inhibitor which can suppress abnormal production of interleukin-6 and can treat the above-described diseases.

DISCLOSURE OF INVENTION

The present invention provides an interleukin-6 production inhibitor or a thrombocytosis inhibitor comprising a methanebisphosphonic acid derivative, an ester thereof, a pharmaceutically acceptable salt thereof, or a hydrate thereof, as an active component, the methanebisphosphonic acid derivative being represented by the general formula (I):

general formula (I)

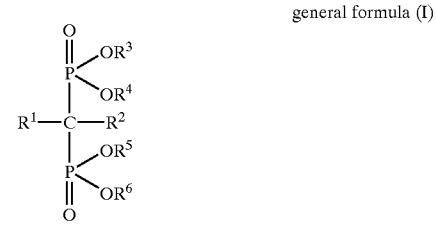

{wherein,
(a)
R$^1$ is hydrogen, a linear or branched alkyl group having 1 to 8 carbon atoms, a hydroxyl group, or a trialkylsiloxy group (wherein the alkyl group is a linear or branched alkyl group having 1 to 8 carbon atoms);
R$^2$ is Ar—A┄ or Het$^1$-A┄ (wherein Ar is an unsubstituted or substituted aryl, Het$^1$ is unsubstituted or substituted 5- or 6-membered monocyclic monoazaaryl, diazaaryl, or thiazaaryl bonded via cyclic carbon atoms, ┄ represents a double or single bond, A is —(D)b-(CH$_2$)c- [(wherein D is sulfur, oxygen, or NR$^7$ (wherein R$^7$ is hydrogen or a linear or branched alkyl group having 1 to 8 carbon atoms), c is an integer of 0 to 3, and b is 0 or 1)] or —CH(=CH)d-CH= (wherein d is 0 or 1, and when A is —(CH=CH)d-CH=, R$^1$ is not present); and
R$^3$, R$^4$, R$^5$, and R$^6$ are each hydrogen, a linear or branched alkyl group having 1 to 8 carbon atoms, or a pharmaceutically acceptable cation, and R$^3$, R$^4$, R$^5$, and R$^6$ may be the same or different; or (b)

R$^1$ is hydrogen or a hydroxyl group, R$^2$ is Ar—B— or Het$^2$-B— (wherein B is alkylene, Ar is the same as above, Het$^2$ is unsubstituted or substituted monoazaaryl, diazaaryl, or thiazaaryl bonded via cyclic carbon atoms or cyclic nitrogen atoms, R$^3$, R$^4$, R$^5$, and R$^6$ are the same as above)}. Production of some other cytokines such as tumor necrosis factor-α (TNF-α), neutrophil chemotactic factors (particularly, interleukin-8 and/or GRO-α), and a monocyte chemotactic factor (MCP-1) is inhibited.

BEST MODE FOR CARRYING OUT THE INVENTION

Examples of the compounds represented by the above general formula (I) are as follows.

The unsubstituted aryl represented by Ar is phenyl, and the substituted aryl is phenyl which is mono- or poly-substituted, e.g. di- or tri-substituted, for example, by lower alkyl, lower alkoxy, lower alkylthio, trifluoromethyl and/or halogen.

The unsubstituted or substituted 5- or 6-membered monocyclic monoazaaryl, diazaaryl, or thiazaaryl bonded via cyclic carbon atoms represented by Het$^1$ is preferably one selected from the group consisting of imidazole-2-yl, imidazole-4-yl, imidazole-5-yl, pyrazole-3-yl, thiazole-4-yl, 2-pyridyl, 3-pyridyl, and 4-pyridyl, and is unsubstituted or substituted by lower alkyl.

The unsubstituted or substituted 5 or 6-membered monocyclic monoazaaryl, diazaaryl, or thiazaaryl bonded via cyclic carbon atoms or cyclic nitrogen atoms represented by Het$^2$ is preferably one selected from the group consisting of pyrolyl, imidazolyl, pyrazolyl, thiazolyl and pyridyl, and is unsubstituted or substituted by lower alkyl.

The bicyclic monoazaaryl, diazaaryl, or thiazaaryl bonded via cyclic carbon atoms or cyclic nitrogen atoms is, for example, imidazo[1,2-a]pyridyl, and preferably imidazo[1,2-a]pyridine-3-yl.

The halogen is, for example, fluoro or bromo, and preferably chloro, but may also be iodo.

The alkylene is preferably lower alkylene, and the Ar-alkyl is, for example, phenyl-lower alkyl, in which the phenyl ring may be substituted, as described above.

The C1 to C8 linear or branched alkyl is, for example, methyl, ethyl, n-propyl, isopropyl, n-butyl, isobutyl, sec-butyl, or tert-butyl. Moreover, the alkyl groups include corresponding pentyl, hexyl and heptyl groups.

The C1 to C8 alkoxy is, for example, methoxy, ethoxy, n-propoxy, isopropoxy, or n-butoxy. Moreover, the alkoxy groups include corresponding pentyloxy, hexyloxy and heptyloxy groups.

The C1 to C8 alkylthio is, for example, methylthio, ethylthio, n-propylthio, isopropylthio, or n-butylthio.

The lower alkylene is a linear or branched C1 to C7 alkylene, such as methylene, ethylene, propylene, butylene, pentylene, hexylene, heptylene, 2-methyl-1,3-propylene, or 2,4- or 1,5-dimethyl-1,5-pentylene.

The groups and compounds,modified by the term "lower" contain up to 8 carbon atoms, and preferably up to 4 carbon atoms.

When A in the general formula (I) is —(D)b-(CH$_2$)c- and when ∶∶ is a single bond, D is sulfur, oxygen, or NR$^7$, (wherein R$^7$ is hydrogen or a linear or branched alkyl group having 1 to 8 carbon atoms), c is an integer of 0 to 3, and b is 0 or 1. More preferably, b and c are independently 0 or 1.

When R$^1$ is a hydroxyl group or a trialkylsiloxy group (wherein the alkyl is linear or branched alkyl having 1 to 8 carbon atoms), when D is sulfur, oxygen, or NR$^7$ (wherein R$^7$ is the same as above), and when b=1, c=0 is not preferable because the compound is unstable. In this case, however, when c is an integer of 1 to 3, the compound is stable and are preferred. Examples of particularly preferable A include CH$_2$, CH$_2$CH$_2$, S, NH, SCH$_2$, SCH$_2$CH$_2$, SCH$_2$CH$_2$CH$_2$, NHCH$_2$, O, and OCH$_2$. A compound in which the phenyl group is directly bonded to a carbon atom of the methanebisphosphonic acid, but not by the A is also included (In this case, b=c=0). The case of A=—(CH=CH) d-CH= indicates that ∶∶ is a double bond and that R$^1$ is not present, wherein d is 0 or 1.

The linear or branched alkyl group having 1 to 8 carbons represented by R$^1$, R$^3$, R$^4$, R$^5$, and R$^6$ is, for example, methyl, ethyl, propyl, isopropyl, butyl, isobutyl, t-butyl, pentyl, hexyl, cyclopentylmethyl, or cyclohexylmethyl. The linear or branched alkyl group having 1 to 8 carbons when R$^1$ is trialkylsiloxy group is the same as above.

Examples of pharmaceutically acceptable cations represented by R$^3$, R$^4$, R$^5$, and R$^6$ include metallic cations, ammonium NR$_4$ (wherein R is hydrogen or a linear or branched alkyl group having 1 to 8 carbons). Examples of particularly preferred cations include cations of alkali metals, e.g., lithium, sodium, and potassium, and alkaline earth metals, e.g., magnesium and calcium. Cations of other metals, such as aluminum, zinc, and iron, are also included in the present invention. Examples of ammoniums include ammoniums of ammonia, primary amines, secondary amines, and tertiary amines, and quarternary ammoniums. Examples of these compounds include ammonium of ammonia, methylamine, dimethylamine, trimethylamine, ethylamine, diethylamine, triethylamine, propylamine, dipropylamine, isopropylamine, diisopropylamine, butylamine, dibutylamine, isobutylamine, t-butylamine, monoethanolamine, diethanolamine, and triethanolamine; tetramethylammonium; and tetraethylammonium. Among these, cations of sodium, potassium, ammonia, and alkylamines are preferable.

In R$^3$ to R$^6$, the cations may be the same or different, and combinations of cations and hydrogen, for example, mono-cation salts, di-cation salts, and tri-cation salts are included in the present invention. Preferably, the methanebisphosphonic acid derivative represented by the general formula (I) is a derivative in which all R$^3$ to R$^6$ are hydrogen atoms, three of R$^3$ to R$^6$ are hydrogen atoms while the remaining one is sodium, three are hydrogen atoms while the remaining one is ammonium, or two are hydrogen atoms and the remaining two are sodium ions, or two are hydrogen atoms and the remaining two are ammonium ions.

The present invention relates to the use of a methanebisphosphonic acid derivative, an ester thereof, a pharmaceutically acceptable salt thereof, or a hydrate thereof, as an interleukin-6 production inhibitor or a thrombocytosis inhibitor, the methanebisphosphonic acid derivative being represented by the general formula (I):

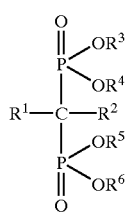

general formula (I)

{wherein,
(a) $R^1$ is hydrogen, a linear or branched alkyl group having 1 to 8 carbon atoms, a hydroxyl group, or a trialkylsiloxy group (wherein the alkyl group is a linear or branched alkyl group having 1 to 8 carbon atoms); $R^2$ is Ar—A--- or $Het^1$-A--- (wherein Ar is an unsubstituted or substituted aryl, $Het^1$ is unsubstituted or substituted 5- or 6-membered monocyclic monoazaaryl, diazaaryl, or thiazaaryl bonded via cyclic carbon atoms, --- represents a double or single bond, A is —(D)b-(CH$_2$)c- [(wherein D is sulfur, oxygen, or $NR^7$ (wherein $R^7$ is hydrogen or a linear or branched alkyl group having 1 to 8 carbon atoms), c is an integer of 0 to 3, and b is 0 or 1)] or —(CH=CH)d-CH= (wherein d is 0 or 1, and when A is —(CH=CH)d-CH=, $R^1$ is not present); and $R^3$, $R^4$, $R^5$, and $R^6$ are each hydrogen, a linear or branched alkyl group having 1 to 8 carbon atoms, or a pharmaceutically acceptable cation, and $R^3$, $R^4$, $R^5$, and $R^6$ may be the same or different; or
(b) $R^1$ is hydrogen or a hydroxyl group, $R^2$ is Ar—B— or $Het^2$-B— (wherein B is alkylene, Ar is the same as above, $Het^2$ is unsubstituted or substituted monoazaaryl, diazaaryl, or thiazaaryl bonded via cyclic carbon atoms or cyclic nitrogen atoms, $R^3$, $R^4$, $R^5$, and $R^6$ are the same as above)}.

Moreover, the present invention relates to the use of a methanebisphosphonic acid derivative, an ester thereof, a pharmaceutically acceptable salt thereof, or a hydrate thereof, as an interleukin-6 production inhibitor or a thrombocytosis inhibitor, the methanebisphosphonic acid derivative being represented by the general formula (I) wherein (a) $R^1$ is hydrogen, a linear or branched alkyl group having 1 to 8 carbon atoms, a hydroxyl group, or a trialkylsiloxy group (wherein the alkyl group is a linear or branched alkyl group having 1 to 8 carbon atoms); $R^2$ is Ar—A--- (wherein Ar is represented by the general formula (II):

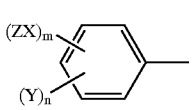

general formula (II)

[wherein Z is a linear or branched alkyl group having 1 to 8 carbon atoms, which may have a substituent group of a nitrogen, oxygen, or silicon atom, a phenyl group having 6 to 15 carbon atoms (which may be substituted by a linear or branched alkyl group having 1 to 8 carbon atoms, a linear or branched alkoxy group having 1 to 8 carbon atoms, a halogen, or a hydroxyl group), or a naphthyl group, X is sulfur, oxygen, or nitrogen, Y is a linear or branched alkyl group having 1 to 8 carbon atoms, a trifluoromethyl group, a halogen, a linear or branched alkenyl group having 2 to 8 carbon atoms, or a cycloalkyl group having 3 to 8 carbon atoms, m is an integer of 0 to 2, and n is an integer of 0 to 2]), or $Het^1$-A--- (wherein $Het^1$ is unsubstituted thiazolyl or pyridyl or a lower-alkyl-substituted thiazolyl or pyridyl), --- represents a double or single bond, and A, $R^3$, $R^4$, $R^5$, and $R^6$ are the same as above; or (b) $R^1$ is hydrogen or a hydroxyl group, $R^2$ is Ar—B— or $Het^2$-B— (wherein B is lower alkylene, Ar is the same as above, $Het^2$ is unsubstituted or lower-alkyl-substituted imidazolyl, pyridyl, or imidazo[1,2-a]pyridyl bonded via cyclic carbon atoms or cyclic nitrogen atoms).

Examples of the substituent groups of the methanebisphosphonic acid devivative having Ar represented by the above general formula (II) are as follows.

Examples of the alkyl groups having 1 to 8 carbon atoms as Z of substituent group ZX, which may have a substituent group of a nitrogen, oxygen, or silicon atom include methyl, ethyl, propyl, isopropyl, butyl, isobutyl, tert-butyl, pentyl, hexyl, cyclobutyl, cyclopentyl, cyclohexyl, cyclopentylmethyl, cyclohexylmethyl, 2-aminoethyl, 2-N-methylaminoethyl, 2-N,N-dimethylaminoethyl, 2-hydroxyethyl, 2-alkoxyethyl, 2-trialkylsiloxyethyl, 2-aminopropyl, 2-N-methylaminopropyl, 2-N,N,-dimethylaminopropyl, 3-aminopropyl, 3-N-methylaminopropyl, 3-N,N-dimethylaminopropyl, 2-hydroxypropyl, 2-alkoxypropyl, and 2-trialkylsiloxypropyl. Other examples of Z are phenyl, substituted phenyl, and naphtyl which have 6 to 15 carbon atoms. Examples of the linear or branched alkyl groups having 1 to 8 carbon atoms as substituent groups of the phenyl group include methyl, ethyl, propyl, isopropyl, butyl, isobutyl, tert-butyl, pentyl, hexyl, cyclopentylmethyl, and cyclohexylmethyl. Examples of the linear or branched alkoxy groups having 1 to 8 carbon atoms include methoxy, ethoxy, n-propoxy, isopropoxy, n-butoxy, pentyloxy, and hexyloxy. The halogens include fluorine, chlorine, bromine, and iodine. The position of the substituent group ZX may be ortho, para, or meta.

Examples of the linear or branched alkyl groups having 1 to 8 carbon atoms in the substituent group Y include methyl, ethyl, propyl, isopropyl, butyl, isobutyl, tert-butyl, pentyl, hexyl, cyclopentylmethyl, and cyclohexylmethyl. Examples of the linear or branched alkenyl groups having 2 to 8 carbon atoms include vinyl, allyl, 1-propenyl, isopropenyl, butenyl, and pentenyl. Examples of the cycloalkyl groups having 3 to 8 carbon atoms include cyclopropyl, cyclobutyl, cyclopentyl, and cyclohexyl. The position of the substituent group Y is not limited. X is sulfur, oxygen, or nitrogen, and m and n are each 0, 1, or 2.

In the methanebisphosphonic acid derivative, the ester thereof, the pharmaceutically acceptable salt thereof, or the hydrate thereof, used as an interleukin-6 production inhibitor or a thrombocytosis inhibitor, preferably, in the general formula (I);
(a) $R^1$ is hydrogen; $R^2$ is unsubstituted or halogen-substituted phenylthio, alkyl-substituted phenylthio, alkoxy-substituted phenylthio, alkylthio-substituted phenylthio, unsubstituted or halogen-substituted phenoxy, alkyl-substituted phenoxy, alkoxy-substituted phenoxy, alkylthio-substituted phenoxy, unsubstituted or halogen-substituted pyridylthio, alkyl-substituted pyridylthio, alkoxy-substituted pyridylthio, or alkylthio-subsituted pyridylthio; and $R^3$, $R^4$, $R^5$, and $R^6$ are the same as above; or
(b) $R^1$ is hydrogen or hydroxy; $R^2$ is $Het^2$-B— (wherein B is C1 to C7 alkylene, $Het^2$ is unsubstituted or lower-alkyl-substituted imidazolyl, pyridyl, or imidazo[1,2-a]pyridyl bonded via cyclic carbon atoms or cyclic nitrogen atoms); and $R^3$, $R^4$, $R^5$, and $R^6$ are the same as above.

In the methanebisphosphonic acid derivative, the ester thereof, the pharmaceutically acceptable salt thereof, or the hydrate thereof, more preferably, in the general formula (I);

(a) $R^1$ is hydrogen; $R^2$ is unsubstituted or chloro-substituted phenylthio, C1 to C8 alkyl-substituted phenylthio, C1 to C8 alkoxy-substituted phenylthio, C1 to C8 alkylthio-substituted phenylthio, unsubstituted or chloro-substituted phenoxy, C1 to C8 alkyl-substituted phenoxy, C1 to C8 alkoxy-substituted phenoxy, or C1 to C8 alkylthio-substituted phenoxy, 2-, 3-, or 4-pyridylthio; and $R^3$, $R^4$, $R^5$, and $R^6$ are the same as above; or (b) $R^1$ is hydrogen or hydroxy; $R^2$ is $Het^2$-B— (wherein B is methylene, ethylene, propylene, or pentylene, $Het^2$ is imidazole-1-yl, imidazole-3-yl, imidazole-4-yl, imidazole-5-yl, 1-methylimidazole-2-yl, 5-methylimidazole-2-yl, 4-methylimidazole-5-yl, 2- or 3-pyridyl, or imidazo[1,2-a]pyridyl-3-yl); and $R^3$, $R^4$, $R^5$, and $R^6$ are the same as above.

In the methanebisphosphonic acid derivative, the ester thereof, the pharmaceutically acceptable salt thereof, or the hydrate thereof, more preferably, in the general formula (I), $R^1$ is hydrogen, a linear or branched alkyl group having 1 to 8 carbon atoms, hydroxy group, or a trialkylsiloxy group (wherein the alkyl group is a linear or branched alkyl group having 1 to 8 carbon atoms); $R^2$ is Ar—A⋮⋮ (wherein Ar is represented by the general formula (II):

general formula (II)

[wherein Z is a linear or branched alkyl group having 1 to 8 carbon atoms, X is sulfur, Y is a linear or branched alkyl group having 1 to 8 carbon atoms, a trifluoromethyl group, a halogen, a linear or branched alkenyl group having 2 to 8 carbon atoms, or a cycloalkyl group having 3 to 8 carbon atoms, m is 1, and n is 0 or 1]), ⋮⋮ represents a single bond, and $R^3$, $R^4$, $R^5$, and $R^6$ are the same as above.

Among the methanebisphosphonic acid derivatives represented by the general formula (I), the esters thereof, the pharmaceutically acceptable salts thereof, or the hydrates thereof, the methanebisphosphonic acids are more preferably selected from 1-hydroxy-2-(imidazole-1-yl)ethane-1,1-bisphosphonic acid, 1-hydroxy-2-(imidazole-3-yl)ethane-1, 1-bisphosphonic acid, 1-hydroxy-2-(imidazole-4-yl)ethane-1,1-bisphosphonic acid, 1-hydroxy-2-(imidazole-5-yl) ethane-1,1-bisphosphonic acid, 1-hydroxy-3-(imidazole-4-yl)propane-1,1-bisphosphonic acid, 1-hydroxy-2-(1-methylimidazole-2yl)ethane-1,1-bisphosphonic acid, 1-hydroxy-2-(4-methylimidazole-5-yl)ethane-1,1-bisphosphonic acid, 1-hydroxy-2-(3-pyridyl)ethane-1,1-bisphosphonic acid, 2-(2-pyridyl)ethane-1,1-bisphosphonic acid, (2-pyridylthio)methane-1,1-bisphosphonic acid, 1-hydroxy-2-(imidazo[1,2-a]pyridine-3-yl)ethane-1,1-bisphosphonic acid, phenoxymethane-1,1-bisphosphonic acid, (4-chlorophenyl)thiomethane-1,1-bisphosphonic acid, (4-methoxyphenyl)thiomethane-1,1-bisphosphonic acid, and (4-methylthiophenyl)thiomethane-1,1-bisphosphonic acid.

In specific embodiments of the present invention of the methanebisphosphonic acid derivatives, the esters thereof, the pharmaceutically acceptable salts thereof, or the hydrates thereof, the methanebisphosphonic acids are selected from 1-hydroxy-2-(imidazole-1-yl)ethane-1,1-bisphosphonic acid, 1-hydroxy-2-(3-pyridyl)ethane-1,1-bisphosphonic acid, 2-(2-pyridyl)ethane-1,1-bisphosphonic acid, (4-chlorophenyl)thiomethane-1,1-bisphosphonic acid, (4-methoxyphenyl)thiomethane-1,1-bisphosphonic acid, (4-methylthiophenyl)thiomethane-1,1-bisphosphonic acid, and 1-hydroxy-2-(imidazo[1,2-a]pyridine-3-yl)ethane-1,1-bisphosphonic acid.

The methanebisphosphonic acid derivative represented by the general formula (I) is known as described above, and can be produced by any known process. For example, the compound in which $R^1$ is hydrogen and $R^2$ is Ar—S— in the formula may be prepared by reacting methanebisphosphonic acid tetra-lower-alkyl ester with disulfide represented by the formula Ar—S—S—Ar in the presence of a strong metallic base, such as NaH and by hydrolyzing the resulting tetra-lower-alkyl ester.

The methanebisphosphonic acid derivative represented by the general formula (I), the ester thereof, the pharmaceutically acceptable salt thereof, or the hydrate thereof in according with the present invention is useful as an in vivo interleukin-6 production inhibitor, and effects thereof are anticipated in the prevention and treatment of diseases related to the interleukin-6, for example, thrombocytosis, inflammatory diseases, abnormal immune response diseases, osteoporosis, rheumatoid arthritis, hypercalcemia, multiple myeloma, cachexia, nephristis, systemic lupus erythematosus, atrial myxoma, Castleman's syndrome, Kawasaki disease, and psoriasis.

The methanebisphosphonic acid derivative represented by the general formula (I), the ester thereof, the pharmaceutically acceptable salt thereof, or the hydrate thereof in accordance with the present invention can suppress an abnormal increase in the number of platelets in blood, and effects thereof are anticipated in the prevention and treatment of thrombocytosis, that is, primary thrombocythemia, secondary thrombocytosis, and reactive thrombocytosis as a thrombocytosis inhibitor, and is useful in the prevention and treatment of thrombosis, such as peripheral ischemia and transient cerebral ischemia; hemorrhagic diseases, such as peliosis, subcutaneous bleeding, nasal bleeding, bloody stool, gingival bleeding, and intracranial bleeding; large artery infarction, such as myocardial infarction and cerebral infarction.

When the methanebisphosphonic acid derivative is used as an interleukin-6 production inhibitor or thrombocytosis inhibitor, this can be used as it is or as a pharmaceutical composition thereof with pharmaceutically acceptable known carrier and vehicles. Administration may be by oral adiminstration, such as by tablets, capsules, powders, granules, pills and syrups; and by parenteral administration, such as by parenteral solutions, ointments, and suppositories. The dosage depends on the object of the administration, the administration route, and disease, and is approximately 0.1 mg to 5 g and preferably approximately 1 mg to 2 g. This dosage is used for oral administration or parenteral administration, once to several times per day, or one time/day to seven days.

The present invention will now be described more specifically with reference to Examples.

EXAMPLES

Example 1

Suppression of Production of Interleukin-6 in Human Peripheral Blood Monocytes

Using (4-methylthiophenyl)thiomethanebisphosphonic acid disodium salt (hereinafter referred to as "Compound 1")

as a test drug, the following pharmacological test was performed. Blood was collected from a healthy human male using heparin as an anticoagulant, and monocytes were separated by a specific gravity centrifugal method. The monocytes were diluted to $2.5 \times 10^6$ cells/ml using a serum-free culture medium (AIM-V), LPS (10 μg/ml) and Compound 1 were added, and culturing was performed in a 5%-$CO_2$ incubator at 37° C. for 24 hours. After the incubation, the supernatant was recovered by centrifugal separation.

The concentration of the interleukin-6 in the recovered culture supernatant was measured using an HS Human IL-6 Immunoassay (made by the R&D Company).

The results of the measurements are shown in Table 1. In Table 1, a value when LPS stimulation was not performed is shown as unstimulated.

TABLE 1

|  | Interleukin-6 Concentration (pg/ml) |
| --- | --- |
| Unstimulated | 160 |
| Only LPS Stimulation | 35,400 |
| LPS Stimulation + Compound 1 ($10^{-4}$ M) | 28,400 |

As shown in Table 1, the production of the interleukin-6 in human peripheral blood monocytes by the LPS stimmulation was suppressed by the addition of Compound 1.

Example 2

Suppression of Interleukin-6 in Rat Adjuvant Arthritis Model

Into 0.1 ml of liquid paraffin was suspended 0.1 mg of *Mycobacterium butyricum* dried inactivated adjuvant, and the suspension was intracutaneously injected into the left hindpaw of Female Lewis rat of 8 weeks old. Compound 1 was dissolved in sterile distilled water as a vehicle and was subcutaneously administered at a rate of 0.5 mg per 1 kg of body weight every day for 2 weeks from the 9th day after the adjuvant treatment. For the control group, the sterile distilled water was subcutaneously administered. Serum was collected on the 37th day after the adjuvant treatment.

The concentration of the interleukin-6 in the collected serum was measured by means of multiplicative activation of the 7TD1 cell, which is a mouse plasmacytoma line cell. That is, the resulting serum was subjected to serial dilution in a 50 ml RPMI1640 culture medium containing 10% fetal bovine serum and 50 μM 2-mercaptoethanol in a 96-well plate. Herein, 50 μl of 7TDI cell suspension ($2 \times 10^4$ cells/ml) was added to each medium. In this state, cells were incubated for 72 hours, and the interleukin-6 activity was determined by the proliferation rate of the cells. The cell proliferation was calculated as the unit number of the interleukin-6 concentration in the sample from the absorbance at 595 nm of a dye formed by reduction by mitochondria of 3-[4,5-dimethylthiazole-2-yl]2,5-diphenyltetrazolium bromide, which was added at the 4th hour before the completion of the incubation, using a calibration curve which was prepared by a standard human interleukin-6 sample (1 pg of protein was defined as 1 unit of activity).

The results of the measurement are shown as the average±standard error in Table 2. Table 2 also shows the results of rats which were not subjected to adjuvant treatment as a nontreated group. In the table, the statistical analysis result (vs. adjuvant nontreated group) according to the Student's T test is indicated by the mark †† (significance level p<0.01), and the statistical analysis result (vs. vehicle administered group) according to the Dunnett's test is indicated by the mark ** (significance level p<0.01).

TABLE 2

|  | Number of Samples | Interleukin-6 Concentration (U/ml) |
| --- | --- | --- |
| Adjuvant Nontreated | 6 | 23.45 ± 23.45 |
| Adjuvant Treatment + Vehicle Administered | 6 | 3,134.15 ± 654.8†† |
| Adjuvant Treatment + Compound 1 Administered | 6 | 179.36 ± 78.16** |

As shown in Table 2, the interleukin-6 concentration in the serum was significantly increased by the adjuvant treatment compared to the adjuvant nontreated group, whereas, in the Compound 1 administered group, interleukin-6 concentration in the serum was significantly decreased.

Example 3

Suppression of Thrombocytosis in Rat Adjuvant Arthritis Model

Into 0.1 ml of liquid paraffin was suspended 0.1 mg of *Mycobacterium butyricum* dried inactivated adjuvant, and the suspension was intracutaneously injected into left hindpaw of Female Lewis rat of 8 weeks old. Compound 1 was dissolved in sterile distilled water as a vehicle and was subcutaneously administered at a rate of 2.5 mg per 1 kg of body weight every day for 4 weeks from the 8th day after the adjuvant treatment. For the control group, the sterile distilled water was subcutaneously administered. Serum was collected on the 36th day after the adjuvant treatment to measure the number of platelets in the peripheral blood.

The results of the measurement are shown as the average±standard error in Table 3. Table 3 also shows the results of rats which were not subjected to adjuvant treatment as a nontreated group. In the table, the statistical analysis result (vs. adjuvant nontreated group) according to the Student's T test is indicated by the mark †\ (significance level p<0.01), and the statistical test result (vs. vehicle administered group) according to the Dunnett's test is indicated by the mark ** (significance level p<0.01).

TABLE 3

|  | Number of Samples | Number of Platelets ($\times 10^4$/μl) |
| --- | --- | --- |
| Adjuvant Nontreated | 6 | 62.0 ± 1.07 |
| Adjuvant Treatment + Vehicle Administered | 6 | 103.9 ± 3.57†† |
| Adjuvant Treatment + Compound 1 Administered | 6 | 74.4 ± 2.32** |

As shown in Table 3, the number of the platelets in the peripheral blood was significantly increased by the adjuvant treatment compared to the adjuvant nontreated group, whereas, in the Compound 1 administered group, significant suppression in the number of the platelets is confirmed.

PHARMACEUTICAL APPLICABILITY

A methanebisphosphonic acid derivative represented by the general formula (I), ester thereof, a pharmaceutically acceptable salt thereof, or a hydrate thereof is useful as an interleukin-6 production inhibitor, and effects thereof are anticipated in the prevention and treatment of diseases relating to the interleukin-6, for example, thrombocytosis, inflammatory diseases, abnormal immune response diseases, osteoporosis, rheumatoid arthritis, hypercalcemia, multiple myeloma, cachexia, and nephritis.

What is claimed is:

1. A pharmaceutical composition comprising an interleukin-6 production inhibitor comprising a methanebisphosphonic acid derivative, an ester thereof, a pharmaceutically acceptable salt thereof, or a hydrate thereof, as an active component, the methanebisphosphonic acid derivative being represented by the general formula (I):

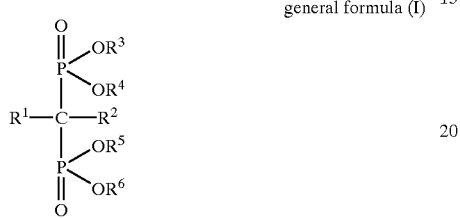

general formula (I)

wherein,
(a) $R^1$ is hydrogen, a linear or branched alkyl group having 1 to 8 carbon atoms, a hydroxyl group, or a trialkylsiloxy group wherein the alkyl group is a linear or branched alkyl group having 1 to 8 carbon atoms; $R^2$ is Ar—A⋯ wherein Ar is represented by the general formula (II):

general formula (II)

wherein Z is a linear or branched alkyl group having 1 to 8 carbon atoms, which may have a substituent group of a nitrogen, oxygen, or silicon atom, a phenyl group having 6 to 15 carbon atoms which may be substituted by a linear or branched alkyl group having 1 to 8 carbon atoms, a linear or branched alkoxy group having 1 to 8 carbon atoms, a halogen, or a hydroxyl group, or a naphthyl group, X is sulfur, oxygen, or nitrogen, Y is a linear or branched alkyl group having 1 to 8 carbon atoms, a trifluoromethyl group, a halogen, a linear or branched alkenyl group having 2 to 8 carbon atoms, or a cycloalkyl group having 3 to 8 carbon atoms, m is an integer of 1 or 2, and n is an integer of 0 to 2, ⋯ represents a double or single bond, A is —(D)b-(CH$_2$)c-((wherein D is sulfur, oxygen, or NR$^7$ (wherein R$^7$ is hydrogen or a linear or branched alkyl group having 1 to 8 carbon atoms), c is an integer of 0 to 3, and b is 0 or 1)) or —(CH=CH) d-CH= (wherein d is 0 or 1, and when A is —(CH=CH)d-CH=, $R^1$ is not present); and $R^3$, $R^4$, $R^5$, and $R^6$ are each hydrogen, a linear or branched alkyl group having 1 to 8 carbon atoms, or a pharmaceutically acceptable cation, and $R^3$, $R^4$, $R^5$, and $R^6$ may be the same or different; or (b) $R^1$ is hydrogen or a hydroxyl group, $R^2$ is Ar—B— wherein B is lower alkylene, Ar is the same as above.

2. The pharmaceutical composition according to claim 1, wherein, in the general formula (I), (a) $R^1$ is hydrogen, $R^2$ is unsubstituted-phenylthio, alkyl-substituted phenylthio, alkoxy-substituted phenylthio, alkylthio-substituted phenylthio, unsubstituted or halogen-substituted phenoxy, alkyl-substituted phenoxy, alkoxy-substituted phenoxy, alkylthio-substituted phenoxy, and $R^3$, $R^4$, $R^5$, and $R^6$ are the same as the definition in claim 1.

3. The pharmaceutical composition according to claim 1, wherein, in the general formula (I), (a) $R^1$ is hydrogen; $R^2$ is unsubstituted phenylthio, C1 to C8 alkyl-substituted phenylthio, C1 to C8 alkoxy-substituted phenlythio, C1 to C8 alkylthio-substituted phenylthio, unsubstituted or chloro-substituted phenoxy, C1 to C8 alkyl-substituted phenoxy, C1 to C8 alkoxy-substituted phenoxy, or C1 to C8 alkylthio-substituted phenoxy; and $R^3$, $R^4$, $R^5$, and $R^6$ are the same as the definition in claim 1.

4. The pharmaceutical composition according to claim 1, wherein, in the general formula (I), $R^1$ is hydrogen, a linear or branched alkyl group having 1 to 8 carbon atoms, hydroxy group, or a trialkylsiloxy group (wherein the alkyl group is a linear or branched alkyl group having 1 to 8 carbon atoms); $R^2$ is Ar—A⋯ (wherein Ar is represented by the general formula (II):

general formula (II)

[wherein Z is a linear or branched alkyl group having 1 to 8 carbon atoms, X is sulfur, Y is a linear or branched alkyl group having 1 to 8 carbon atoms, a trifluoromethyl group, a halogen, a linear or branched alkenyl group having 2 to 8 carbon atoms, or a cycloalkyl group having 3 to 8 carbon atoms, m is 1, and n is 0 or 1]), ⋯ represents a single bond, and A, $R^3$, $R^4$, $R^5$, and $R^6$ are the same as the definition in claim 1.

5. A method of treating a target disease in a mammal comprising administrating in vivo to said mammal, a therapeutically effective amount of an interleukin-6 production inhibitor according to any one of claims 1 to 4, wherein said target disease is an inflammatory disease or an abnormal immune response disease.

6. A method of treating a target disease in a mammal by in vivo administration to said mammal, a therapeutically effective amount of an interleukin-6 production inhibitor according to any one of claims 1 to 4 wherein said target disease is osteoporosis, rheumatoid arthritis, hypercalcemia, multiple myeloma, cachexia, nephritis, or systemic lupus erythematosus.

7. A method of treating a target disease in a mammal by in vivo administration to said mammal, a therapeutically effective amount of a thrombocytosis inhibitor containing the methanebisphosphic acid derivative according to any one of claims 1 to 4, or the ester, salt, and hydrate thereof, as an active component, wherein said target disease is thrombocytosis.

8. A pharmaceutical composition comprising an interleukin-6 production inhibitor comprising (4-methylthiophenyl)thiomethane-1,1-bisphosphonic acid, an ester thereof, or a pharmaceutically acceptable salt or hydrate thereof.

9. A pharmaceutical composition comprising an interleukin-6 production inhibitor comprising (4-methylthiophenyl)thiomethane bisphosphonic acid dialkali metal salt, an ester thereof, or a pharmaceutically acceptable salt or hydrate thereof.

10. A method of treatment of a disease in a mammal related to interleukin-6 which comprises the step of in vivo administration of a pharmaceutically effective amount of a composition defined in claim 8, thereby inhibiting interleukin-6 production.

11. A method of treatment of disease in a mammal related to interleukin-6 which comprises the step of in vivo administration of a pharmaceutically effective amount of a composition defined in claim 9, thereby inhibiting interleukin-6 production.

* * * * *